(12) United States Patent
Saggau et al.

(10) Patent No.: US 7,706,584 B2
(45) Date of Patent: Apr. 27, 2010

(54) RANDOM ACCESS HIGH-SPEED CONFOCAL MICROSCOPE

(75) Inventors: Peter Saggau, Houston, TX (US); Vivek Bansal, Houston, TX (US); Saumil Patel, Houston, TX (US)

(73) Assignee: Baylor College of Medicine and William Marsh Rice University, Houston, TX (US)

( * ) Notice: Subject to any disclaimer, the term of this patent is extended or adjusted under 35 U.S.C. 154(b) by 1169 days.

(21) Appl. No.: 10/531,554

(22) PCT Filed: Oct. 22, 2003

(86) PCT No.: PCT/US03/35441

§ 371 (c)(1),
(2), (4) Date: Nov. 10, 2005

(87) PCT Pub. No.: WO2004/038461

PCT Pub. Date: May 6, 2004

(65) Prior Publication Data

US 2006/0140462 A1    Jun. 29, 2006

Related U.S. Application Data

(60) Provisional application No. 60/420,379, filed on Oct. 22, 2002.

(51) Int. Cl.
*G06K 9/00* (2006.01)
(52) U.S. Cl. .................................................. 382/128
(58) Field of Classification Search .......... 382/128–133; 359/210, 204, 209, 305, 385–386, 740, 317, 359/318; 356/318, 417, 317; 250/458.1, 250/459.1, 461.1, 461.2, 234; 600/476, 473, 600/180, 182, 160
See application file for complete search history.

(56) References Cited

U.S. PATENT DOCUMENTS

| 5,760,951 | A | * | 6/1998 | Dixon et al. | ................. 359/385 |
| 6,072,624 | A | * | 6/2000 | Dixon et al. | ................. 359/385 |
| 6,687,035 | B2 | * | 2/2004 | Knebel et al. | ............ 359/204.1 |
| 6,750,963 | B2 | * | 6/2004 | Sampas | ....................... 356/318 |

FOREIGN PATENT DOCUMENTS

| EP | 0284136 | 9/1988 |
| EP | 0466979 | 1/1992 |

OTHER PUBLICATIONS

Bansal, Vivek, et al; Development of a Novel Confocal Microscope for Functional Recording of Fast Neuronal Activity; Proceedings of the Second Joint EMBS/BMES Conference, Houston, Texas, Oct. 23-26, 2002; pp. 2099-2100.

European Search Report for Application No. 03779480 and Annex thereto, dated Apr. 23, 2007, 3 pages.

Computer Generated Translation of EP 0466979, 4 pages.

* cited by examiner

*Primary Examiner*—Sherali Ishrat
(74) *Attorney, Agent, or Firm*—Fish & Richardson P.C.

(57) ABSTRACT

Disclosed herein is a confocal imaging system for imaging a specimen. The system comprises a light source, a light deflector capable of positioning a beam of light produced by the light source at one of a series of predetermined points on the specimen, an addressable spatial filter capable of selectively filtering light from the specimen, and a central processing unit capable of providing selective position control to the light deflector and the addressable spatial filter.

13 Claims, 9 Drawing Sheets

RANDOM ACCESS HIGH-SPEED CONFOCAL MICROSCOPE

SPONSORED RESEARCH OR DEVELOPMENT

This material is based in part upon work supported by the Texas Advanced Research (Advanced Technology/Technology Development and Transfer) Program under Grant Nos. 004949-076 and 004949-065.

REFERENCE TO COMPUTER PROGRAM LISTING APPENDIX

Appendix A includes a printout of a computer program entitled "registration.cpp", "registration.h", and "regtable.m", which are incorporated herein by reference.

BACKGROUND OF THE INVENTION

1. Field of the Invention

The present invention generally relates to confocal microscopy. More particularly, the invention relates to increasing the scanning rate capability of confocal microscopes.

2. Description of Related Art

Confocal microscopy is a technique that allows visualization of small structures in light scattering material such as brain slices. It accomplishes this by combining point illumination with point detection. The point detection is achieved by using a pinhole in an image plane that serves to filter light from out-of-focus planes above and below the area of interest thereby creating an optical section of a relatively thick specimen.

The main limitation of confocal microscopes is the speed of image acquisition, since every image is reconstructed on a point-by-point basis. Typical commercial systems, which rely on relatively slow galvanometer-driven mirrors to position the point illumination, have frame rates of approximately 1 Hz. Even the fastest systems, which scan several illumination spots simultaneously, can only record at approximately 200 Hz. One way that the slower systems are used for faster recording is by only collecting data from the pixels lying on a single line, but even this line-scan technique, which sacrifices flexibility in picking sites-of-interest, only boosts the effective frame rate to approximately 400 Hz. With the majority of current systems, faster imaging time is directly related to shorter dwell times at each site-of-interest, which reduces the achievable signal-to-noise ratio. To achieve the frame rate necessary for making functional recordings at several user-selected sites-of-interest, it is beneficial to have an addressable system that can selectively visit several sites on a specimen without spending any time scanning over areas that do not contain structures of interest.

The use of acousto-optic deflectors (AODs) can increase the speed at which the point illumination may be positioned and allows for random access scanning at user-selected sites-of-interest. However, the use of AODs necessitates a path of light returning from the specimen that is different than the illumination path and thus prevents the use of a stationary pinhole. This in turn requires a pinhole or filter that is spatially and temporally synchronized with the scanning excitation spot. Although there are existing systems that utilize an AOD, those systems only utilize an AOD to reposition the illumination point in one dimension. The deflection of the illumination point in the second dimension is accomplished by a relatively slow galvanometer-driven mirror such as one used on typical confocal microscopes. In addition, the existing systems that utilize an AOD employ a slit in the direction that the AOD deflects the illumination point, rather than a pinhole, thereby preventing true confocal imaging.

There exists, therefore, a need for a confocal microscope that permits flexibility in selecting sites-of-interest with increased scanning and recording rates for observing high-speed phenomena without reducing dwell time at each site-of-interest. Furthermore, to enable accurate site selection, the same system should be able to collect full frame confocal images.

SUMMARY OF THE PREFERRED EMBODIMENTS

In a preferred embodiment, the present invention comprises a random-access confocal microscope. Such a device is necessary for scanning only selected sites-of-interest in a specimen without the time requirements of scanning many sites and only using the results from the sites-of-interest. In order to achieve a faster sampling rate, it is advantageous to only scan selected sites-of-interest. Additionally, by only scanning at selected sites-of-interest, the dwell time at each site is much longer for a given frame rate than with a system that must scan the entire field. Further, such high speed scanning is necessary to observe some phenomena. One example of such phenomena is signal processing and transmission in neurons, although the present invention will have useful application in other fields involving high-speed phenomena as well.

The present microscope comprises a light source, a high-speed light deflector, a central processing unit (CPU), and an addressable spatial filter. The light source may be any collimated light source used for such a microscope, such as a laser. The high-speed light deflector preferably is an acousto-optic deflector (AOD); however, a spatial light modulator such as the digital micromirror device (DMD) from Texas Instruments may also be used. The AOD allows a higher proportion of the source light to be directed to the site-of-interest and thus is preferred. The AOD is connected to the CPU, such that the CPU determines where a beam of light from the light source is directed. The CPU may be any conventional processor that is capable of transmitting controlling signals to the high-speed light deflector and the addressable spatial filter. The addressable spatial filter is controlled by the CPU and is synchronized with the high-speed light deflector to allow simultaneous illumination and detection of a site-of-interest.

The addressable spatial filter may comprise a variety of arrangements that allow random-access detection of a point site-of-interest. The sites may be specified by a user after viewing a full frame confocal image of a specimen. The addressable spatial filter is not necessarily a physical pinhole, as commonly used on previous confocal microscopes. In one embodiment, the addressable spatial filter is comprised of a DMD and a separate photodetector (such as a photodiode or photomultiplier tube). In a second embodiment, the addressable spatial filter is comprised of a complementary metal oxide semiconductor (CMOS) camera. The DMD provides an array of microscopic mirrors that can be actuated individually, allowing actuation of only mirrors corresponding to the location of the site-of-interest. The actuation of these mirrors will direct the returning fluorescence, reflection, or transmission of light from the sites-of-interest in the focal plane to the photodetector. Alternatively, a CMOS camera is capable of reading only designated pixels corresponding to sites-of-interest. Additionally, the CMOS camera allows individual pixel readout without the time delay of conventional imaging systems such as CCD cameras. Both the DMD and CMOS embodiments camera allow high-speed random access imaging of all sites-of-interest at greater than or equal to 1 kHz.

In another embodiment, the present invention provides a method for acquiring optical recordings. The method comprises selecting at least one site-of-interest, configuring a high-speed light deflector to illuminate the at least one site-of-interest, configuring an addressable spatial filter to record the fluorescence, reflection or transmission of light from the at least one site-of-interest, and recording the light from the at least one site-of-interest.

The method may further comprise sequentially selecting and illuminating a plurality of sites-of-interest. The method may still further comprise repeating the previous steps at a frequency greater than or equal to 500 Hz per frame.

In still another alternate embodiment, the present invention comprises optical recordings created using the previously described apparatus and method for acquiring an image.

BRIEF DESCRIPTION OF THE DRAWINGS

For a more detailed understanding of the preferred embodiments, reference is made to the accompanying Figures, wherein.

DETAILED DESCRIPTION OF THE PREFERRED EMBODIMENTS

Figure 1:
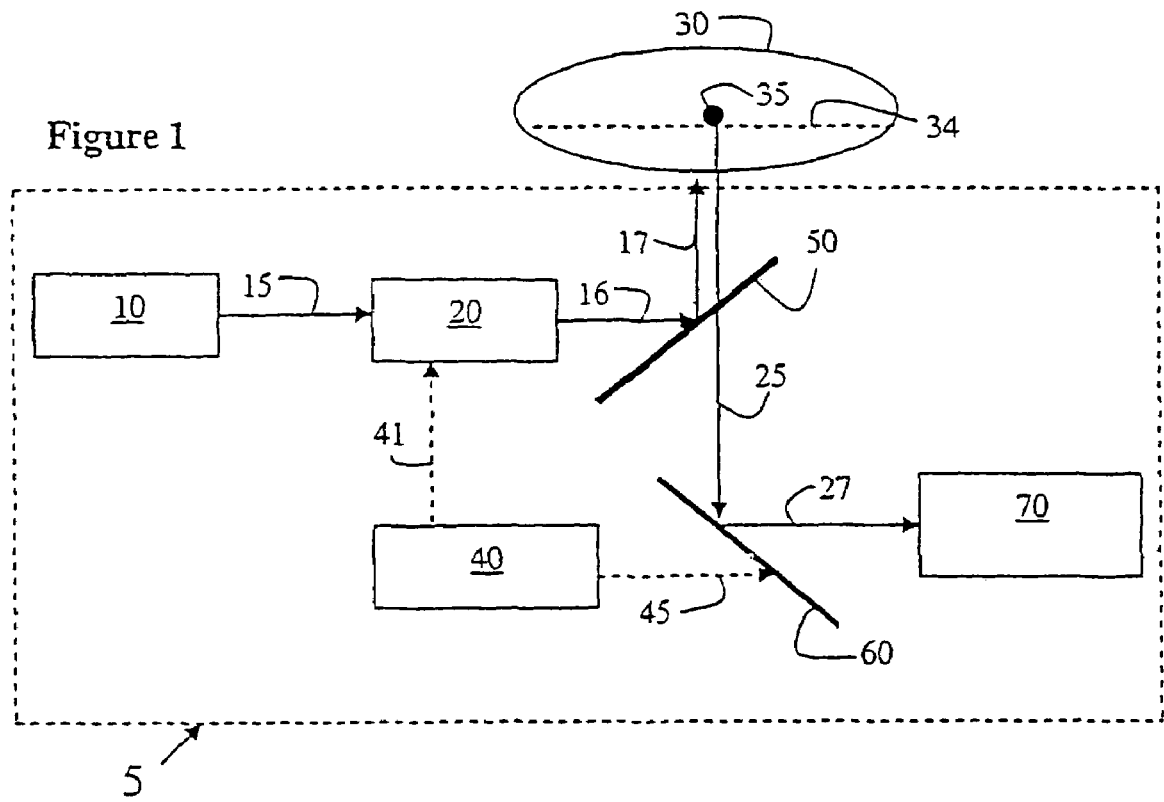
FIG. 1 is a schematic diagram of a confocal microscope constructed in accordance with a first embodiment of the present invention utilizing a DMD as an addressable spatial filter in conjunction with a separate photodetector.

Referring initially to FIG. 1, a random access high-speed confocal microscope 5 includes a laser 10 that emits a light beam 15. Light beam 15 is rapidly redirected by an acousto-optic deflector 20. The new position of light beam 15 is shown in FIG. 1 as a light beam 16, which is reflected by a beam splitter 50 (such as a dichroic mirror in the case of fluorescence) as a light beam 17 onto a specimen 30. After light beam 16 is directed onto the specimen 30, a light beam 25 may be fluoresced, reflected, or transmitted by the specimen 30. The manner in which light beam 25 is produced will depend upon the composition of the specimen and any exogenous optical indicators that might be in use. Light beam 25 from the specimen 30 passes through a beam splitter 50 (such as a dichroic mirror in the case of fluorescence) and to a digital micromirror device (DMD) 60. A central processing unit (CPU) 40 is connected to AOD 20 and sends an electronic signal 41 to control where light beam 15 from laser 10 is directed. CPU 40 also controls the angular position of individual micromirrors in DMD 60 by sending an electronic signal 45. Light beam 25 from a site-of-interest 35 is reflected by the DMD 60 as a light beam 27 to a photodetector 70. Site-of-interest 35 preferably lies on focal plane 34 within specimen 30.

AOD 20 allows for almost instant positioning of light beam 15 emitted from light source 10 because AOD 20 does not have the inertia associated with typical galvanometer-driven mirrors used in conventional confocal microscopes. This increases the speed at which specimen 30 can be scanned for sites-of-interest 35. The scan rate is much higher than typical confocal microscopes, because both AOD 20 and DMD 60 do not have the inertia associated with conventional mirrors and can therefore move directly from one site to the next without scanning over intervening sites.

Figure 1A:
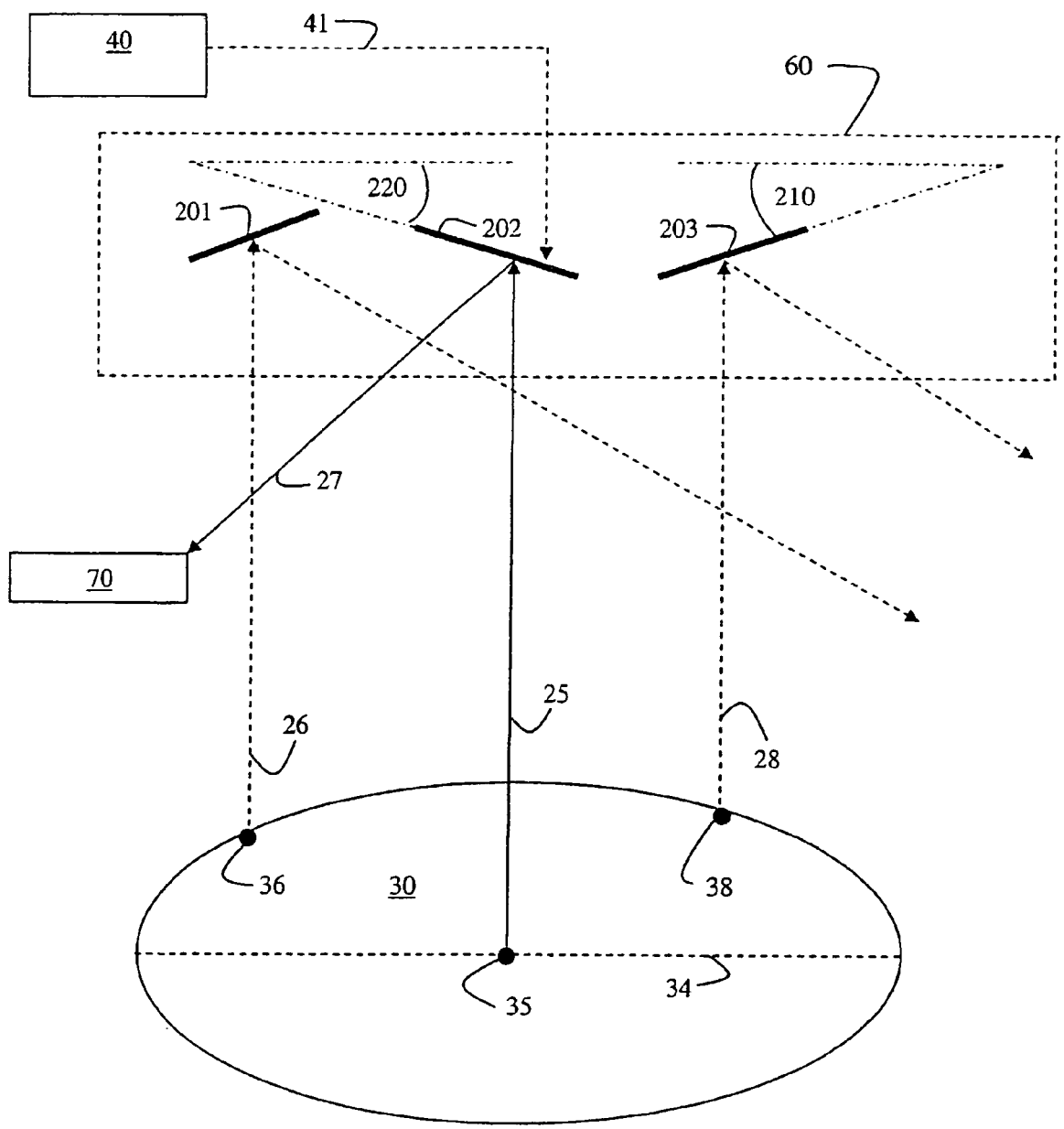
FIG. 1A is a schematic diagram of a DMD with mirrors in a first angular position that reflects light away from a photodetector and a second angular position that reflects light towards a photodetector.

FIG. 1A illustrates schematically how DMD 60 functions as an addressable spatial filter. DMD 60 is preferably an electro-opto-mechanical chip made by Texas Instruments and consists of an array of micromirrors 201, 202, and 203. Micromirrors 201-203 are in a first angular position 210 unless a signal 45 is sent from CPU 40 causing one or more of the micromirrors to change to a second angular position 220. In FIG. 1A, micromirror 202 has been moved to angular position 220 in response to a signal 45 sent by CPU 40. Micromirrors 201-203 are extremely small squares (approximately 16 µm, or 0.000016 meters per side). This allows micromirrors 201-203 to change from first angular position 210 to second angular position 220 very quickly (approximately 20 µs, or 0.000020 seconds). When micromirror 202 is in second angular position 220, light beam 25 from a site-of-interest 35 on specimen 30 is reflected as a light beam 27 to photodetector 70. In the process of focusing light beam 17 onto a site-of-interest 35 in FIG. 1, some light shines on areas above and below the site-of-interest 35. These areas are illustrated as sites-of-non-interest 36 and 38 in FIG. 1A. Micromirrors 201 and 203 remain in angular position 210 and reflect light beams 26 and 28 from sites 36 and 38 that are not of interest. In angular position 220, micromirrors 201 and 203 reflect light beams 27 and 28 away from photodetector 70. CPU 40 synchronizes DMD 60 and AOD 20 so that only micromirror 202 corresponding to a site-of-interest 35 illuminated by light beam 17 (shown in FIG. 1) will reflect a light beam 25 to the photodetector 70. The computer program listing appendix includes programs for synchronizing DMD 60 and AOD 20.

Numerous sites-of-interest 35 may be selected and scanned sequentially while sampling all the sites-of-interest 35 at greater than or equal to 500 Hz. The sampling rate may be as low as the video rate of 20-30 Hz, but preferably it is higher, such as 3 kHz, and more preferably 4 kHz. Most preferably, the sampling rate is 25,000/n, where n is the number of sites-of-interest 35. Thus, for 6 sites-of-interest 35, the sampling rate is 4.167 kHz. This number is based on the demonstrated ability of the present invention to sample a site-of-interest 35 every 40 µs. Furthermore, the system is adaptive so that the number of sites studied simultaneously can be optimized to the type of signal. To study fast signals, fewer sites-of-interest 35 can be selected and to study slower signals, more sites-of-interest 35 can be simultaneously studied.

Figure 2:
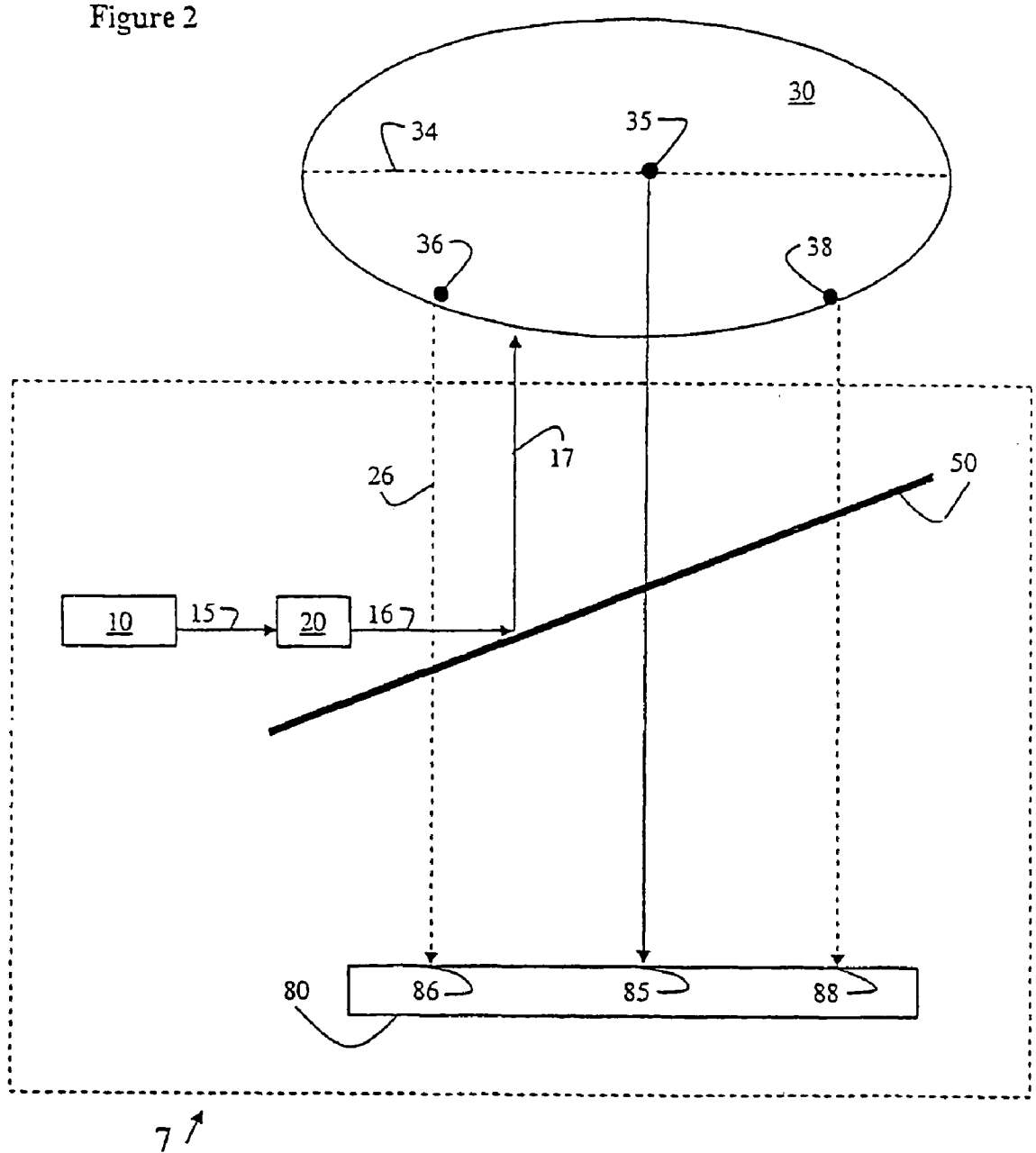
FIG. 2 is a schematic diagram of a confocal microscope constructed in accordance with a second embodiment of the present invention embodiment utilizing a CMOS camera as both an addressable spatial filter and photodetector.

A second embodiment of the present invention is shown schematically in FIG. 2. The random access high-speed confocal microscope 7 shown in FIG. 2 utilizes a complementary metal oxide semiconductor (CMOS) camera 80 in place of the DMD 60 and photodetector 70 used in FIG. 1. In FIG. 2, laser 10 emits light beam 15, which is rapidly re-directed by AOD 20. The new position of light beam 15 is shown in FIG. 2 as light beam 16, which is reflected by beam splitter 50 as light beam 17 onto specimen 30. Light beam 25 from a site-of-interest 35 on specimen 30 passes through beam splitter 50 and to CMOS camera 80. As in the first embodiment, central processing unit (CPU) 40 is connected to AOD 20 and sends electronic signal 41 to control where light beam 15 from laser 10 is directed. CMOS camera 80, which functions as an addressable spatial filter, is also connected to CPU 40. CMOS camera 80 is synchronized with AOD 20 to allow simultaneous illumination and detection of a site-of-interest 35 on specimen 30. Light beam 25 from specimen 30 is received by CMOS camera 80, which is comprised of multiple pixels 85, 86, and 88. CMOS camera 80 allows for individual pixel readout without the time delay of conventional imaging systems. CPU 40 sends an electronic signal 47 to CMOS camera 80 to read only pixels corresponding to a site-of-interest 35. Therefore, only pixel 85 that corresponds to light beam 25 from site-of-interest 35 will be read by CPU 40. Pixels 86 and 88, which correspond to light beams 26 and 28 from sites 36 and 38 that are not of interest, will be ignored by CMOS camera 80. Because only pixel 85 corresponding to site-of-interest 35 is read by CMOS camera 80, the rate at which specimen 30 may be scanned is increased.

Figure 3:
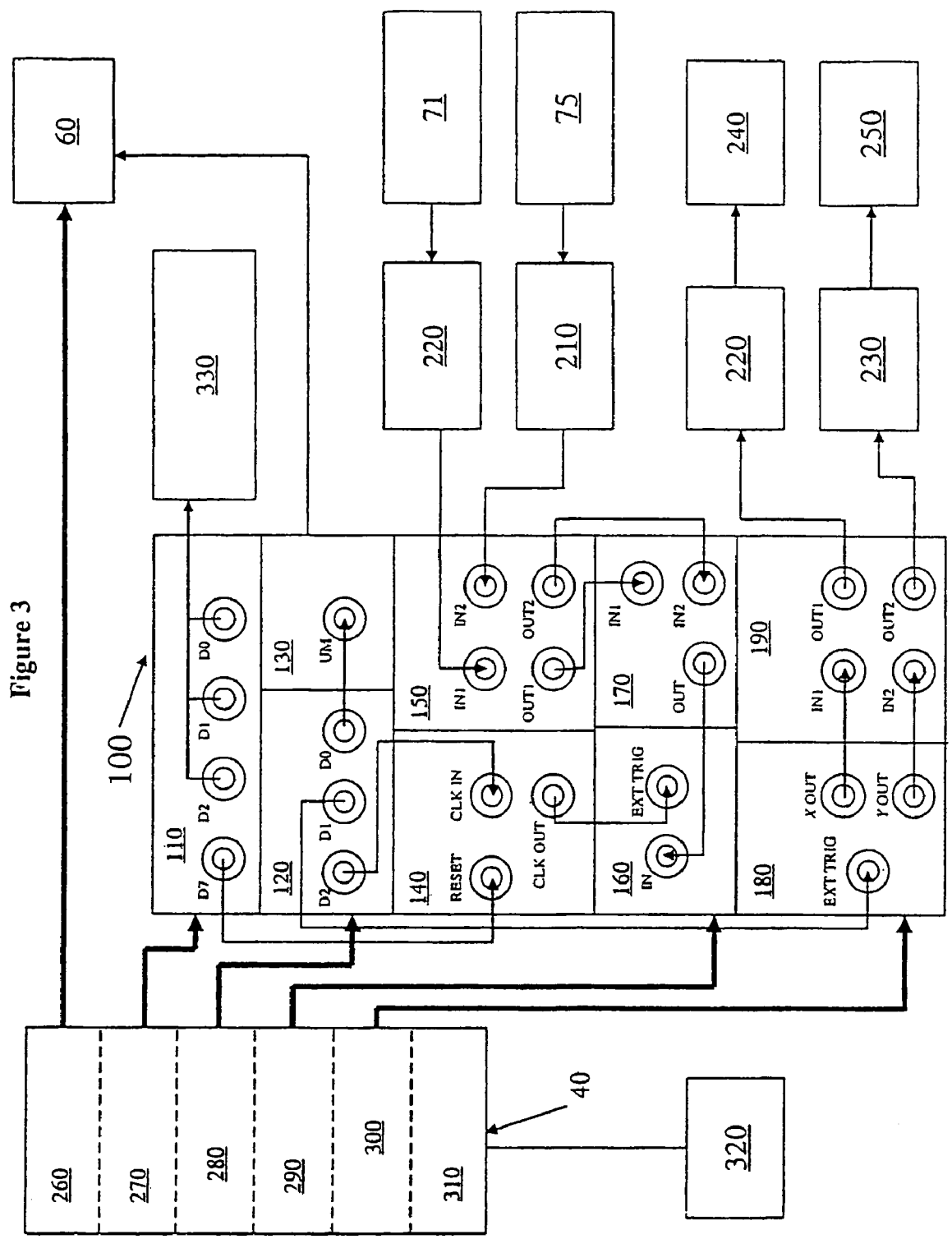
FIG. 3 is a schematic diagram of the electronic components in a first embodiment utilizing a DMD as an addressable spatial filter in conjunction with a separate photodetector.

FIG. 3 illustrates schematically a more detailed layout of electronic components utilized in one embodiment in which the addressable spatial filter comprises DMD 60 and a signal photodiode 71. This configuration is merely one example of numerous variations of electronic components that may be utilized in the present invention and is not intended to limit the scope of the present invention. In addition to CPU 40 and DMD 60, an electronics rack 100 is shown to include several components. CPU 40 contains a parallel port 260, a parallel port 270, a digital input/output card 280, an analog-to-digital converter (ADC) controller 290, a digital-to-analog converter (DAC) 300, and a frame grabber 310. A video camera 320 is preferably connected to frame grabber 310. Video camera 320 is utilized for visualization of the specimen and for rough alignment of the components, while frame grabber 310 is used to display images from video camera 320. Electronics rack 100 preferably contains a parallel port breakout 110, a digital input/output breakout 120, a DMD control 130, a trigger doubler 140, a voltage amplifier 150, an ADC converter 160, a multiplexer 170, a DAC breakout 170, and an analog signal conditioner 190. In addition to signal photodiode 71, there is a reference photodiode 75. The output of signal photodiode 71 is sent to a current-to-voltage converter 200, while the output of reference photodetector 75 is sent to a separate current-to-voltage converter 210. There are also two separate AODs, 240 and 250, for deflection of the illumination beam (light beam 15 in FIG. 1) in both the x- and y-axes. AOD 240 is controlled by AOD driver 220 and AOD 250 is controlled by AOD driver 230. Finally, a stepper motor controller 330 is used for controlling the position of the focal plane 34 within the specimen 30 (both shown in FIG. 1).

Various inputs and outputs of the components are illustrated in FIG. 3. Included below is a summary of the components and the functions served by each. DAC 300 is used to send addresses of the position of light beam 15 (shown in FIG. 1) to AOD 240 and AOD 250. Analog signal conditioner 190 is used to make the voltage output range of DAC breakout 180 optimally match the necessary inputs for AOD driver 220 and AOD driver 230. Parallel port 260 sends addresses for all sites-of-interest 35 (shown in FIG. 1) to DMD 60. Digital input/output 280 controls cycling of the DAC addresses 180 and DMD 60 from one site-of-interest to the next site-of-interest and generates triggers for ADC 160. As illustrated in FIG. 1, light beam 25 from specimen 30 is received by photodetector 70 (shown as photodiode 71 in FIG. 3). In addition, noise from laser 10 is measured with reference photodetector 75. The output signal from signal photodiode 71 passes through current-to-voltage converter 200 and the output signal from reference photodetector 75 passes through current-to-voltage converter 210. The outputs of signal photodiode 71 and reference photodetector 75 are then amplified by voltage amplifier 150. Multiplexer 170 (with sample and hold function capability) is then used to simultaneously sample signal photodiode 71 output and reference photodetector 75 output, which is then sent to ADC 160. Trigger doubler 140 is used to generate two ADC 160 triggers for each given pulse. ADC 160 uses the first trigger to digitize the output from signal photodiode 71 and the second trigger to digitize the output from reference photodetector 75 and then store the results in CPU 40. The signal photodetector output 70 can then be divided by the reference photodetector output 75 to remove the effects of noise from laser 10. Finally, parallel port 270 sends an output to stepper motor controller 330 (used for focusing) and a reset of trigger doubler 140.

Figure 4:
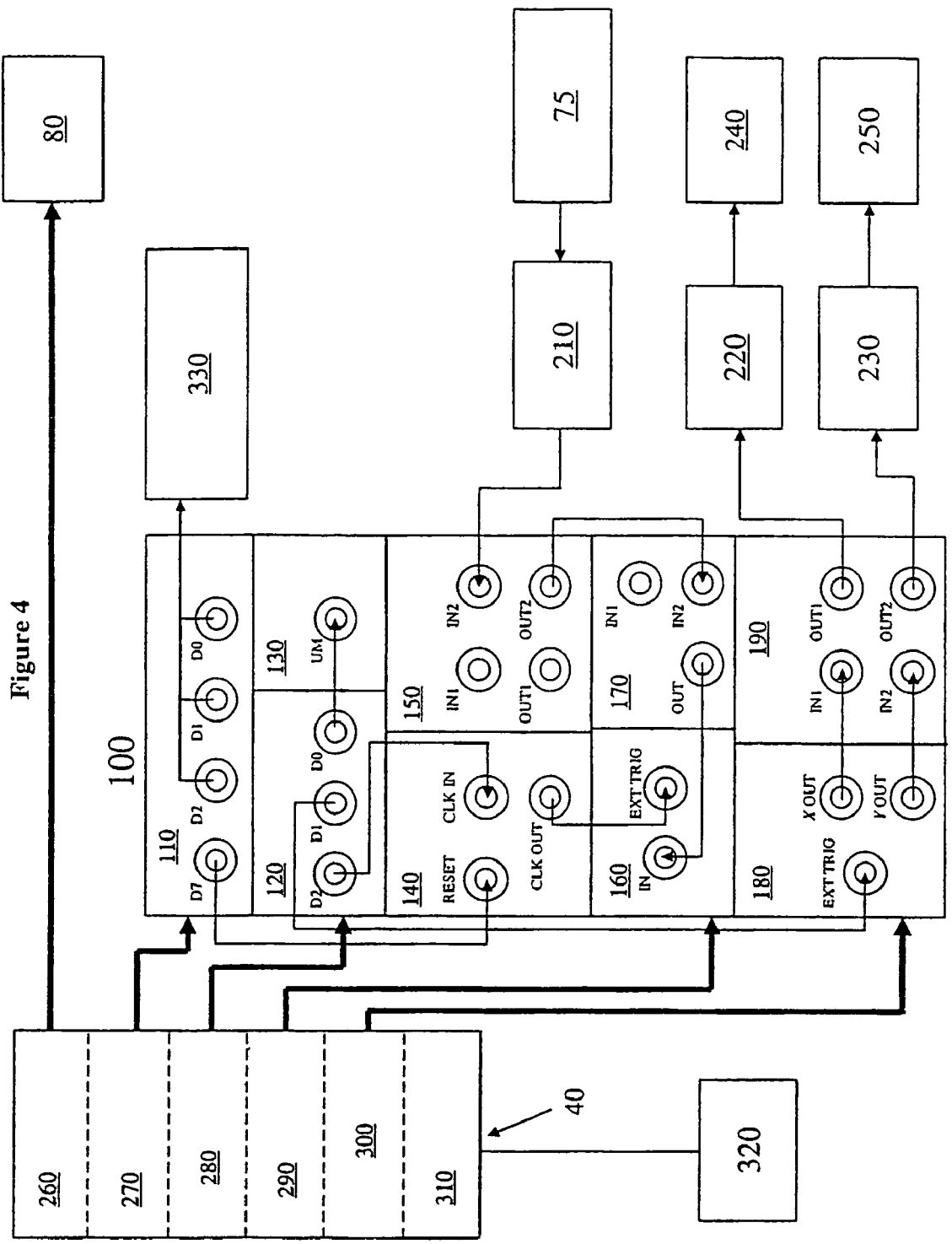
FIG. 4 is a schematic diagram of the electronic components in a second embodiment utilizing a CMOS camera as both an addressable spatial filter and photodetector.

FIG. 4 illustrates schematically another example of the electronic components utilized in an embodiment incorporating a CMOS camera 80 in place of DMD 60 and signal photodiode 71 (shown in FIG. 3). This configuration is merely one example of numerous variations of electronic components that may be utilized in the present invention and is not intended to limit the scope of the present invention. Because the CMOS camera 80 does not need a separate photodetector, signal photodiode 71 is eliminated, as well as current-to-voltage converter 200. An additional difference between the components utilized in FIG. 3 and FIG. 4 is that CMOS camera 80 is controlled by digital input/output 265, instead of parallel port 260. All other electronic components shown in FIG. 4 (and their functions) correspond to those described in FIG. 3.

Figure 5:
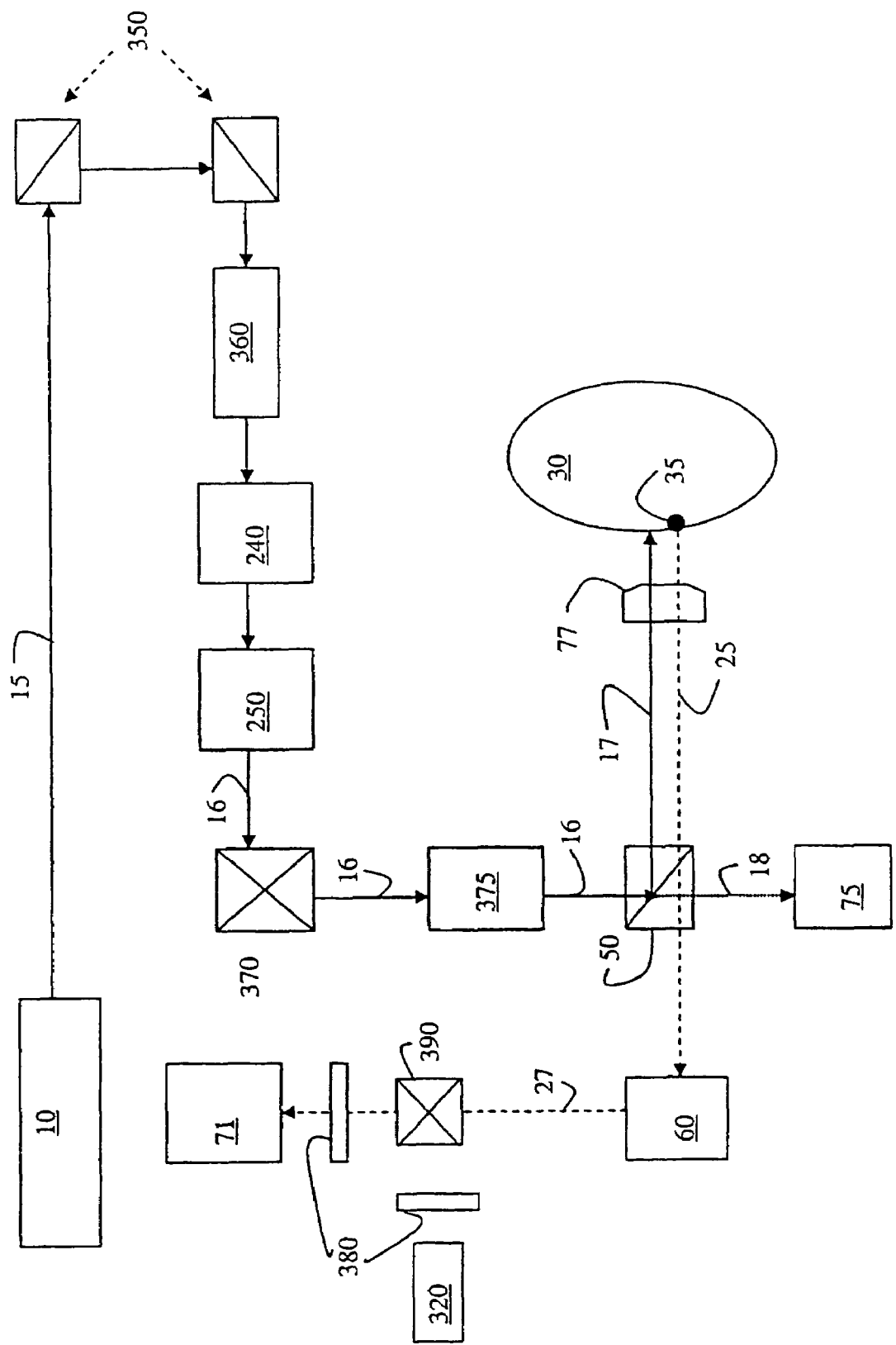
FIG. 5 is a schematic diagram of the optical components in a first embodiment utilizing a DMD as an addressable spatial filter in conjunction with a separate photodetector.

FIG. 5 illustrates a view of the optical components utilized in another embodiment of the present invention incorporating an addressable spatial filter comprising DMD 60 and signal photodiode 71. In this figure, laser 10 emits light beam 15. A beam aligner 350 centers light beam 15 before light beam 15 passes through beam expander 360 and AOD 240 and AOD 250. AOD 240 and AOD 250 position light beam 15, and light beam 16 exits AOD 240 and 250. Beam aligner 370 then directs light beam 16 into demagnification bench 375, which controls the range of scanning for AOD 240 and AOD 250 and the final size of light beam 17 on specimen 30. Light beam 16 is directed to beam splitter 50, which reflects the short wavelength light beam 16 but passes the longer wavelength light beam 25 from the specimen 30. If the wavelengths of light beam 16 and light beam 25 are the same (such as when light beam 25 is reflected from the specimen 30 rather than fluoresced), a polarizing filter and quarter wave plate (not shown) may be used in place of the beam splitter 50 to separate illumination beam 16 from reflected beam 25.

Light beam 16 is reflected by beam splitter 50 as light beam 17, which is focused by objective lens 77 onto specimen 30. A portion 18 of light beam 16 passes through beam splitter 50 and is used to measure fluctuations in the power output of laser 10 with reference photodiode 75. Light beam 25 from specimen 30 is collected by objective lens 77, passes through beam splitter 50 and is received by DMD 60. As shown in FIG. 1A, light beam 25 is reflected off DMD 60 as light beam 27 to photodetector 70. In FIG. 5, a signal photodiode 71, which is used to make optical recordings, is shown as one example of a photodetector 70. In addition, a switch mirror 390 can direct light beam 27 away from signal photodiode 71 and to a video camera 320, which can be used for visualization of specimen 30 and rough alignment of the components. Emission filters 380 ensure that only the desired wavelengths of light beam 27 are detected.

Figure 6:
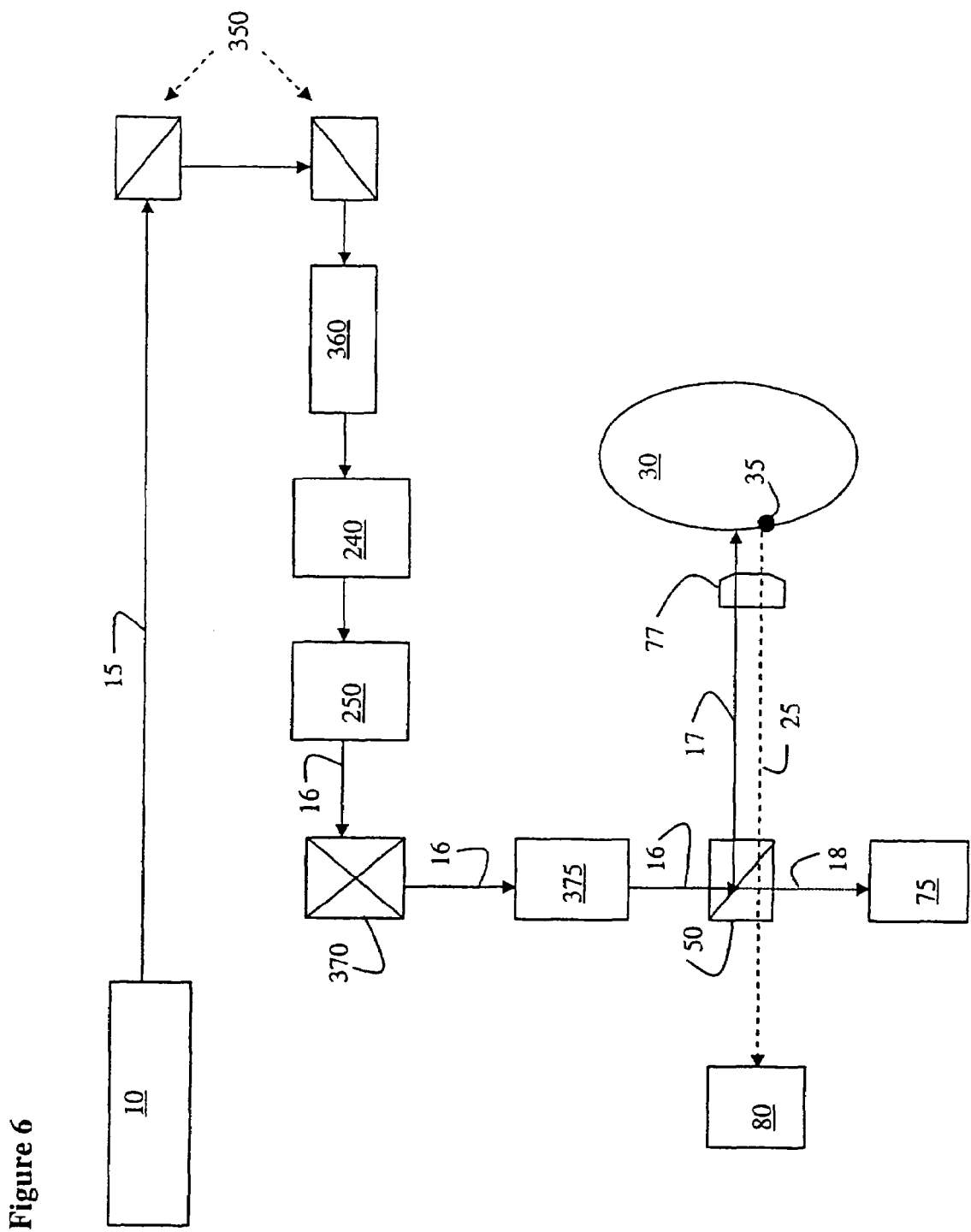
FIG. 6 is a schematic diagram of the optical components in a second embodiment utilizing a CMOS camera as both an addressable spatial filter and photodetector.

FIG. 6 represents a view of the optical components in an embodiment utilizing a CMOS camera 80 as both an addressable spatial filter and photodetector. In FIG. 6, the CMOS camera 80 has replaced DMD 60, signal photodiode 71, and video camera 320. All other optical components remain identical to those found in FIG. 5.

Figures 7, 8:
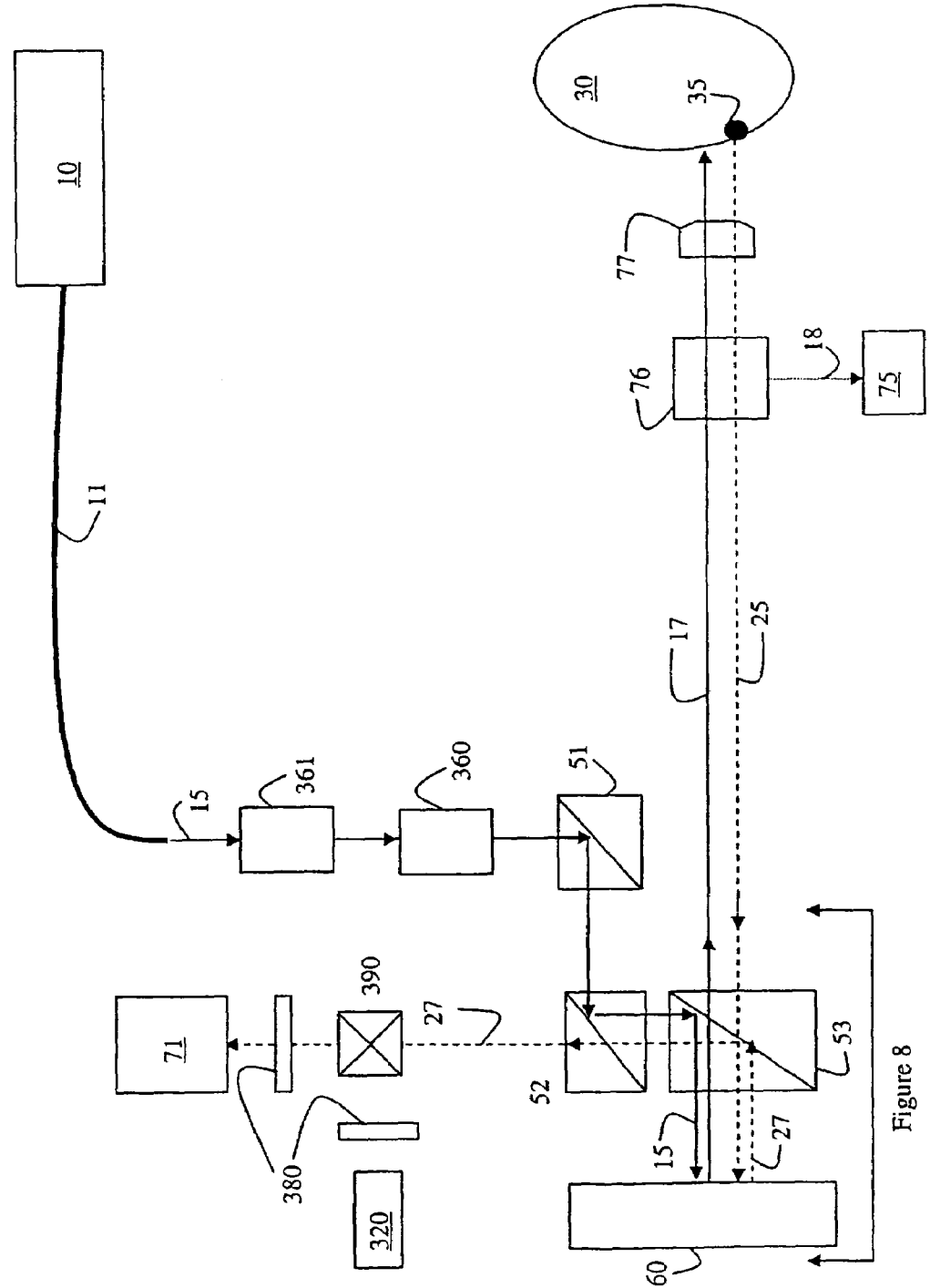
FIG. 7 is a schematic diagram of the optical components in a third embodiment utilizing a DMD as both a high-speed light deflector and an addressable spatial filter.
FIG. 8 is a schematic diagram of optical components in a third embodiment utilizing a DMD as both a high-speed light deflector and an addressable spatial filter.
Figure 8:
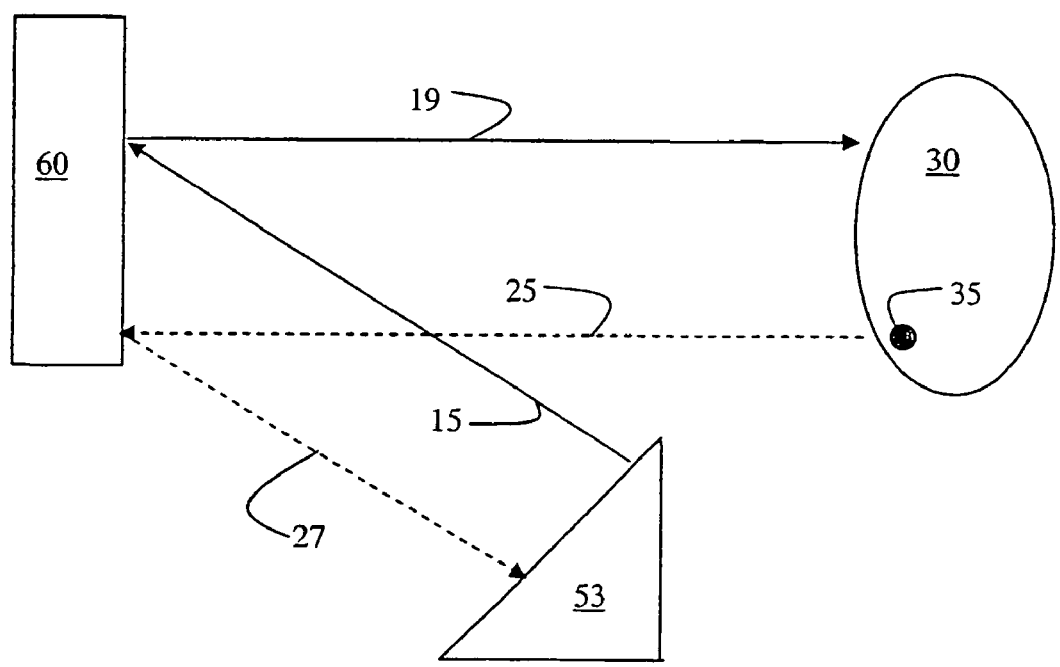

FIG. 7 represents a view of the optical components in an embodiment utilizing a DMD 60 as both a high-speed light deflector and an addressable spatial filter. In FIG. 7, the AODs 240 and 250 (shown in FIG. 5 and 6) have been eliminated because DMD 60 is now used to position light beam 17, which is focused by objective lens 77 onto specimen 30. In FIG. 7, laser 10 emits a light beam 15 via fiber optic cable 11. Light beam 15 first passes through a collimator 361 and then beam expander 360. Light beam 15 then hits a first mirror 51 and is directed to a beam splitter 52, a third mirror 53, and DMD 60. A portion of the microscopic mirrors (not shown) in the DMD 60 are turned on so that some amount of the light from light beam 15 is re-directed as short-wavelength light beam 19 to the specimen 30 and a site-of-interest 35. As best illustrated in FIG. 8, it should be noted that mirror 53 is not on the sane elevation as DMD 60 and specimen 30. Therefore, light beam 19 bypasses mirror 53. A portion 21 of light beam 19 is diverted by a beam splitter 76 and is used to measure fluctuations in the power of laser 10 with reference photodiode 75. Light beam 25 from specimen 30 also bypasses mirror 53 and is received by DMD 60. As shown in FIG. 1A, light beam 25 is reflected off DMD 60 as light beam 27. In FIG. 7, light beam 27 is directed downward to mirror 53 (into the plane of the paper as drawn FIG. 8) and then reflected so that it passes through beam splitter 52 and to a photodetector. In FIG. 7, a signal photodiode 71, which is used to make optical recordings, is shown as one example of a photodetector 70. In addition, a switch mirror 390 can direct light beam 27 away from the signal photodiode 71 and to a video camera 320, which can be used for visualization of the specimen and rough alignment of the components. Emission filters 380 ensure that only the desired wavelengths of light beam 27 are detected.

FIG. 8 represents a front view of DMD 60, mirror 53, and specimen 30 (as shown in FIG. 7). From this view, it is clear that DMD 60 and specimen 30 are arranged so that light beams 19 and 25 bypass mirror 53 and do not pass through mirror 53.

The above discussion and Figures are meant to be illustrative of the principles and various embodiments of the present invention. Numerous variations and modifications will become apparent to those skilled in the art once the above disclosure is fully appreciated. For example, by placing the point detection components (i.e. CMOS 80 or DMD 60 and photodetector 70) on the side opposite the specimen 30 from the illumination beam of light 17, the amount of light transmitted and absorbed by the specimen 30 may be observed. The present invention may also be used in aspects of high-speed imaging other than signal processing and transmission in neurons. It is intended that the following claims be interpreted to embrace all such variations and modifications. Sequential recitation of steps in the claims is not intended to require that the steps be performed sequentially, or that one step be completed before commencement of another step.

The present disclosure hereby incorporates by reference U.S. Pat. No. 5,587,832 (Krause), U.S. Pat. No. 4,893,008 (Horikawa), U.S. Pat. No. 4,863,226 (Houpt et al.), U.S. Pat. No. 4,662,746 (Hornbeck), U.S. Pat. No. 6,084,229 (Pace et al.), and U.S. Pat. No. 4,827,125 (Goldstein) in their entirety, except to the extent they conflict with the present disclosure.

The present disclosure also hereby incorporates by reference, except to the extent that it conflicts with the present disclosure, the paper entitled "A High-Speed Confocal Laser-Scanning Microscope Based on Acousto-Optic Deflectors and a Digital Micromirror Device" by V. Bansal, S. Patel, P. Saggau. This paper was presented and published at the 25th Annual International Conference of the IEEE Engineering in Medicine and Biology Society (held Sep. 17-21, 2003).

What is claimed is:

1. A confocal imaging system for imaging a specimen comprising:
  a light source;
  a light deflector capable of positioning a beam of light produced by the light source at one of a series of predetermined points on the specimen;
  an addressable spatial filter capable of selectively filtering light from the specimen; and
  a central processing unit capable of providing selective position control to the light deflector and the addressable spatial filter.

2. The confocal imaging system according to claim 1, wherein the addressable spatial filer is a complementary metal oxide semiconductor camera.

3. The confocal imaging system according to claim 1, wherein the addressable spatial filter is digital micromirror device.

4. The confocal imaging system according to claim 1, wherein the light deflector is an acousto-optic deflector.

5. The confocal imaging system according to claim 1, wherein the light deflector is a digital micromirror device.

6. The confocal imaging system according to claim 1, wherein the specimen fluoresces, reflects, or transmits light that is received by the addressable spatial filter in response to the light beam from the light source being positioned on the specimen.

7. The confocal imaging system according to claim 6, wherein a user can select at least one site-of-interest on the image of the specimen.

8. The confocal imaging system according to claim 7, wherein the central processing unit controls the light deflector to position the light beam onto the at least one site-of-interest selected by the user.

9. The confocal imaging system according to claim 8, wherein:
  the central processing unit spatially and temporally synchronizes the light deflector and the addressable spatial filter so that the light beam from the light source is directed to the at least one site-of-interest;
  light that is fluoresced, reflected, or transmitted from the at least one site-of-interest is permitted to pass through the addressable spatial filter; and
  light that is fluoresced, reflected, or transmitted from a site that is not of interest is filtered out by the addressable spatial filter.

10. The confocal imaging system according to claim 9, wherein the central processing unit scans the at least one site-of-interest at a frame rate greater than or equal to 500 Hz.

11. The confocal imaging system according to claim 9, wherein the central processing unit scans the at least one site-of-interest at a frame rate greater than or equal to 1 kHz.

12. The confocal imaging system according to claim 9, wherein the central processing unit scans the at least one site-of-interest at a frame rate greater than or equal to (25,000/n) Hz, where "n" is equal to the number of sites-of-interest.

13. The confocal imaging system according to claim 1, wherein the system is capable of collecting a full frame confocal image of the specimen.

* * * * *